Figure 1:
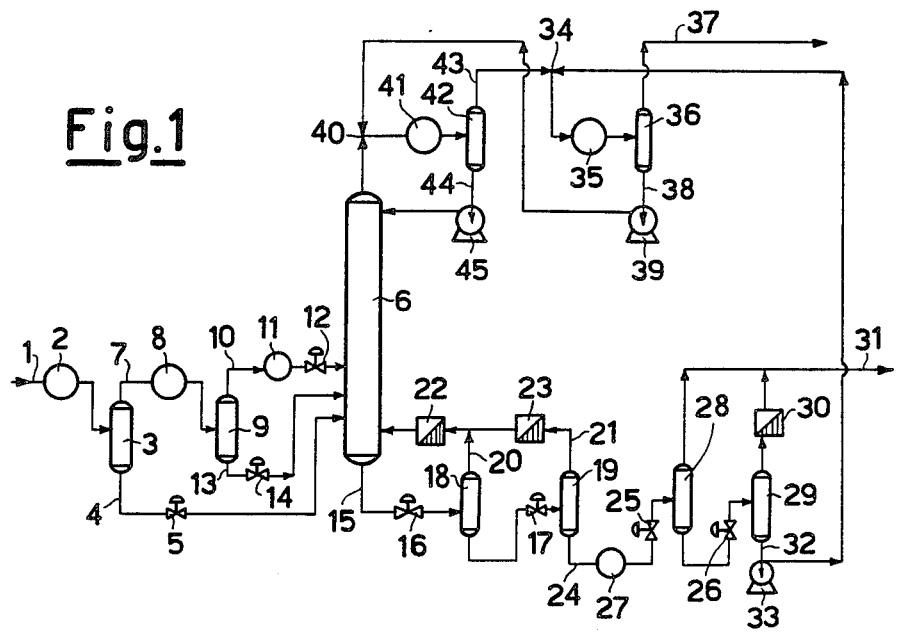

United States Patent [19]

Gazzi et al.

[11] Patent Number: 4,710,210

[45] Date of Patent: Dec. 1, 1987

[54] CRYOGENIC PROCESS FOR THE REMOVAL OF ACIDIC GASES FROM MIXTURES OF GASES BY USING SOLVENTS

[75] Inventors: Luigi Gazzi, Milan; Carlo Rescalli, San Donato Milanese, both of Italy

[73] Assignee: Snamprogetti, S.p.A., Milan, Italy

[21] Appl. No.: 863,875

[22] Filed: May 16, 1986

[30] Foreign Application Priority Data

May 24, 1985 [IT] Italy ................... 20890 A/85

[51] Int. Cl.$^4$ ................................ F25J 3/02
[52] U.S. Cl. ......................... 62/17; 55/68; 55/73; 62/20
[58] Field of Search ............. 62/17, 20; 55/68, 73

[56] References Cited
U.S. PATENT DOCUMENTS 4,097,250  6/1978  Pagani et al. .................. 62/31
4,305,733 12/1981  Scholz et al. .................. 62/17

Primary Examiner—Ronald C. Capossela
Attorney, Agent, or Firm—Morgan & Finnegan

[57] ABSTRACT

Cryogenic process for the removal of acidic gases from natural gases or from synthesis gases essentially comprising the absorption in one or more towers in order to reduce the content of acidic gases, a cooling carried out, in the case of one single absorber tower, upstream the same tower, or, in case of two absorber towers, between the same towers, a regeneration of the solvent or of the solvents used in the absorption, the solvent or the solvents used being selected among low molecular weight esters, alcohols and ethers, characterized in that with the solvent or solvents the gas outcoming from one or more of the absorber towers is mixed once or more times, the mixtures thus formed being then cooled, the solvent being thus separated from the same gas.

6 Claims, 2 Drawing Figures

CRYOGENIC PROCESS FOR THE REMOVAL OF ACIDIC GASES FROM MIXTURES OF GASES BY USING SOLVENTS

The present invention relates to a process for the removal of acidic gases such as hydrogen sulphide and carbon dioxide from mixtures of gases containing them, particularly suitable to the use for the treatment of gas mixtures with even very high concentrations of acidic gases.

The processes of the prior art for the solution of such problem are technically suitable to handle gases which in their raw state contain relatively low percentages of acidic gases.

They suffer indeed from the fact of having been developed in a situation in which energy was relatively cheap and only natural gases having low contents of such components were hence exploited.

Such processes of the prior art can be used also for the processing of gases containing high concentrations of acidic components, but with unacceptable consequences of financial, and to the limit, of also technical character.

Such processes are in fact essentially based on the absorption with selective solvents, which retain the acidic components, thus leaving the gas purified.

The cost of such treatment results thus proportional, with good approximation, to the amount of solvent which is used relatively to the amount of gas to be processes.

Such an amount of solvent is an increasing function of the content in acidic components.

The treatment cost must then be attibuted to the purified gas.

It is hence clear that the treatments according to the prior art have unacceptably increasing costs with increasing contents of acidic gases.

In the present energetic situation, it is necessary to be able to exploit to the best the resources available.

To start up the production of gas fields with gases having a high content of acidic gases, or to the purpose of purifying the synthesis gases produced by starting from fuel oil or from coal, therefore the need presently exists of having available treatment processes suitable to handle gases with high and very high contents of acidic components, able to yield products with even very strict specification.

The treatment of such gases requires the adoption of mixed cryogenic and solvent-using technologies, so as to combine the advantages of both technologies, a good purification of the gases with acceptable costs being obtained.

The same Applicant has already claimed a process of such a type by the U.S. Pat. No. 4,097,250 granted on June 27, 1979. In such patent, the purification is reported of a raw gas containing more than 70% of acidic gases, by the combined use of a low-temperature distillation, and of absorption by solvent.

The solvents described are dimethylether polyethyleneglycol and propylene carbonate.

Always the same Applicant has disclosed in the U.S. Pat. No. 4,561,869 granted on Dec. 31, 1985 and U.S. Pat. No. 4,591,370 granted on May 27, 1987, a process wherein the regenerated solvent is mixed with the gas outcoming from the absorber tower and is cooled in a heat exchanger before being fed to the absorber tower.

It has been found now a new purification cryogenic process particularly suitable to the treatment of gases containing high contents of acidic gases, by means of which the circulation of solvent is considerably reduced.

The process being the object of the present invention, which comprises essentially an absorption in one or more absorber towers in order to reduce the content of acidic gases, a cooling carried out, in the case of one single absorber tower, upstream the same tower; or, in case of two absorber towers, between the same towers; a regeneration of the solvent or of the solvents used in the absorption, is characterized in that the gas outcoming from one or more of the absorber towers is mixed once or more times with the solvent or solvents, the mixtures thus formed being then cooled, the solvent or solvents being thus separated from the same gas.

The solvents of the process according to the invention are substantially low molecular weight alcohols, esters and ethers belonging to the following classes:

Esters of alcohols of general formula $R_1COOR_2$, wherein $R_1$ and $R_2$ are alkyl groups of from 1 to 4 carbon atoms, equal to or different from each other, wherein one or more hydrogen atoms can be substituted by alcoholic groups, such as methyl formate, methyl acetate, ethyl acetate, monoethyleneglycol acetate.

Esters of glycols of general formula:

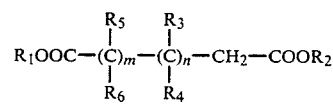

or

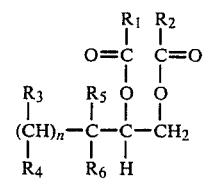

wherein $R_1$ and $R_2$ are alkyl groups having from 1 to 4 carbon atoms, equal to or different from each other, $R_3$, $R_4$, $R_5$, $R_6$, equal to or different from each other, are either alkyl groups containing from 1 to 3 carbon atoms or hydrogen atoms, m and n are integers which can have the value 0 or 1, such as 1,3-propanediol diacetate, 2,2-dimethyl-1,3,-propanediol diacetate, 1,2-propanediol diacetate, monoethyleneglycol diacetate.

Cyclic esters (lactones) of formula

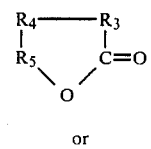

or

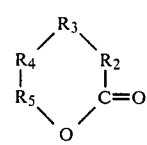

wherein $R_2$, $R_3$, $R_4$, $R_5$, equal to or different from each other, are alkylene groups wherein one or more hydrogen atoms can also be substituted by alkylic, alcoholic or ether groups, such as butyrolactone, caprolactone.

Alcohols of general formula

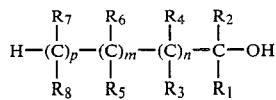

wherein $R_1$, $R_2$, $R_3$, $R_4$, $R_5$, $R_6$, $R_7$, $R_8$, equal to or different from each other, are alkyl groups having from 1 to 3 carbon atoms or hydroxy groups or hydrogen atoms, m, n and p are integers which can assume the values 0 and 1, such as monoethyleneglycol, diethyleneglycol, 1,2-propanediol, 1,3-propanediol, 1,4-butanediol, methanol, ethanol, propanol, isopropanol, n-butanol, isobutanol, sec-butanol, tert-butanol.

Cyclic ethers such as

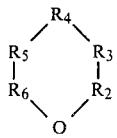

wherein $R_2$, $R_5$, $R_6$, equal to or different from each other, are alkylene groups wherein hydrogen can also be substituted by alkyl or methoxy groups, $R_3$ can be either an oxygen atom or an alkylene group wherein hydrogen can also be substituted by alkyl or methoxy groups, $R_4$ can be either equal to $R_3$ or can be absent in case of a pentaatomic ring, such as tetrahydrofuran, methyltetrahydrofuran, tetrahydropyran, 1,3-dioxolane, 2-methoxy-1,3-dioxolane, 1,4-dioxane.

Ethers of general formula

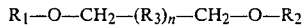

$$R_1-O-CH_2-(R_3)_n-CH_2-O-R_2$$

wherein $R_1$ represents an alkyl group of from 1 to 4 carbon atoms, $R_2$ is either an alkyl group of from 1 to 4 carbon atoms or a hydrogen atom, $R_3$ is either an alkylene group or ($CH_2-O-CH_2$), n is an integer which can have the value 0 or 1, such as 1,2-dimethoxyethane, 1,2-methoxyethoxyethane, dimethoxydiethyleneglycol, monomethoxydiethyleneglycol.

Ethers of general formula

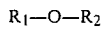

$$R_1-O-R_2$$

wherein $R_1$ and $R_2$, either equal to or different from each other, are alkyl groups of from 1 to 4 carbon atoms, wherein one or more hydrogen atoms can be substituted by alcoholic groups such as ethyl ether, propyl ether, 1-methoxyethanol, 1-methoxy-2-propanol, 1-methoxy-3-propanol, ethoxyethanol.

Ester-ethers, compounds containing both the functions, of formula:

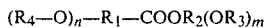

$$(R_4-O)_n-R_1-COOR_2(OR_3)_m$$

wherein $R_3$ and $R_4$, equal to or different from each other, are alkyl groups having from 1 to 4 carbon atoms, $R_2$ is an alkylene or alkyl group having from 1 to 4 carbon atoms, $R_1$ is either equal to $R_2$ or equal to $R_3$, m and n are integers which can have the value 0 or 1, such as methyl 2-methoxyethylacetate or methyl methoxyacetate or ethyl methoxyacetate.

The above reported solvents have a combination of several properties particularly favourable for their use as selective solvents.

They have indeed a high stability under the use conditions, high solvent power for the acidic gases, high selectivity for $H_2S$ and $CO_2$ relatively to hydrocarbons, low molecular weight and low melting point. This last characteristic is essential for the application in a cryogenic process.

In the case of the processing of natural gas, after the condensation at low temperature and before the end absorption by solvent, the gas is available at low temperatures, considerably lower than 0° C.

During the end absorption, it is useful to be able to reach temperatures considerably lower than the gas temperature, which are very favourable, because in this way the absorption power of the solvent and its selectivity increase. The solvents of the process according to the invention show low melting point and are hence particularly suitable for use in a cryogenic process.

The solvents according to the invention can be used alone or mixed with each other, or to them water and/or an organic compound having low melting point and/or low viscosity and/or low molecular weight, such as dimethyl ether, methanol, acetone, toluene, ethanol, propane, butane, pentane can be added, to the purpose of adjusting their solvent characteristics as a function of the gas to be treated and of its pressure and temperature conditions.

The organic compound can be added in proportions comprised within the range of fron 0.3 to 40% by weight relatively to the weight of the resulting mixture, and water can be added up to a maximum of 10% by weight.

Going back to the process, the mixings between the gas outcoming from the absorber tower or towers and the solvent or solvents are preferably carried out in a mixer by feeding said streams in countercurrent to each other.

Said mixings are, for each gas outcoming from an absorber tower, as previously said, in a number higher than 1, and are preferably in a number of two.

In case the gas, or each gas outcoming from one absorber tower undergoes two mixings, such mixings can be carried out in the following way: first, a mixing of the gas being treated with the regenerated solvent or solvents takes place, and then to said mixing a cooling and a separation follows of the mixture obtained, thus from the gas the solvent or solvents being separated, which solvent os solvents is/are in its/their turn mixed in a second mixing step with the gas leaving the absorber tower. To said second mixing step a cooling and a separation follows of the mixture obtained in said second mixing, from the gas, which is fed to the first mixing, the solvent or solvents, which is/are fed to the absorber tower, being separated.

The two coolings following the two mixings can be carried out at the same temperature or at different temperatures, preferably within a temperature range between $-30°$ and $-100°$ C., and more preferably between $-40°$ and $-80°$ C.

The cooling of the natural gas or synthesis gas can take place in a heat exchanger by vapourizing a portion of the acidic gases contained in the $CO_2$-rich solvent in a suitable point of the regeneration.

The cooling of the gas can also take place inside the absorber tower.

The solvent or solvents used for the absorption of the acidic gases in the absorber tower can be regenerated first by means of one or more expansion steps (at maximum, three of such steps) from which above all the valuable components co-absorbed in the first absorber tower, or in the single absorber tower, are recovered, then by means of one or more further expansion steps (at maximum, four of such steps), from which mainly the acidic gases evolve.

The solvents thus regenerated are recycled to the absorber tower or absorber towers after being mixed with the gas as described above.

The regeneration of the mixture must be completed by a distillation tower if in the acidic gases also $H_2S$ is contained, because the specifications as for residual $H_2S$ in the treated gas are much more limitative than for $CO_2$ only; whilst if in the acidic gases only $CO_2$ is contained, using or not using a distillative regeneration tower depends on the maximum allowed $CO_2$ content in the purified gas.

Always in case the regeneration tower is present, a portion of the mixture leaving the expansion steps can be sent to the regeneration tower, whilst the other portion, not completely regenerated, can be recycled to the absorber tower.

The valuable components which evolve from the expansions of the solvent rich in acidic gases are compressed, cooled and recycled to the absorber tower.

The expansions of the solvent rich in acidic gases can be carried out in an expansion valve, or, at least partly, in a turbine.

The regeneration by expansion of the solvent rich in acidic gases can be integrated with the heating of the same solvent, to the purpose of favouring the removal of the acidic gases by evaporation and recover cooling power to be used in the process.

The expansion steps from which mainly acidic gases evolve can be from 1 to 4, producing streams of acidic gases under progressively lower pressures, of which, one or two can be kept under vacuum, in which case the acidic gases evolved must be compressed again. In some cases, on the contrary, operating under vacuum is not necessary, because the end pressure is a function of the temperature reached and of the purification level desired.

The mainly acidic gases containing streams produced under high pressures can be expanded by means of an expansion valve, or of a turbine, to the delivery pressure, to the purpose of producing work and refrigerating effect.

The absorber tower or towers operates/operate under a pressure comprised within the range of from 20 to 110 kg/cm$^2$ and at a temperature comprised within the range of from $-100°$ C. to $40°$ C. In case the distillation tower for the regeneration of the solvent is present, said tower shall operate under a pressure comprised within the range of from 0.1 to 5 kg/cm$^2$ and at a head temperature comprised within the range of from $-60°$ C. to $10°$ C. and at a bottom temperature comprised within the range of from $10°$ C. to $200°$ C.

Figure 2:
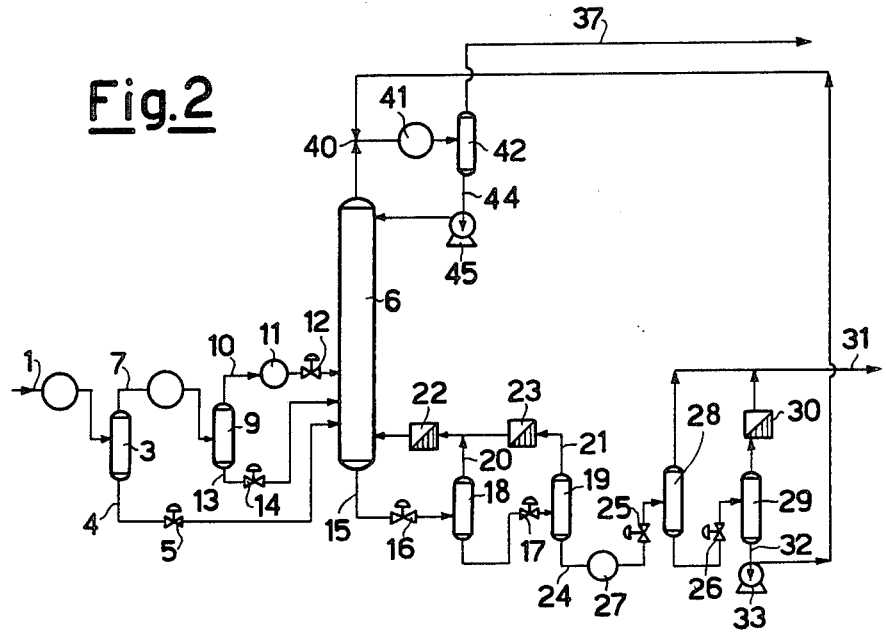

The invention shall be now better described by referring to the flow sheets of attached FIGS. 1 and 2, which show preferred forms of embodiment, which however must not be considered as limitative of the same invention.

The raw gas is supplied to the plant by the piping 1, is cooled and partly condensed in 2 and is then sent to the separator 3 the liquid 4, which through the valve 5 is fed to the absorber tower 6, being separated from the not condensed gas 7. The not condensed gas 7 is cooled and partly condensed in 8 and is sent to the separator 9 from which the gas 10 not condensed in 8 evolves, and is fed, after being cooled in 11, to the absorber tower 6 through the valve 12, whilst the liquid 13 is fed in its turn, through the valve 14, to the absorber tower 6.

In the heat exchangers 2, 8 and 11, the heat exchange can be carried out by taking advantage of the cooling power of the process streams.

From the bottom of the absorber tower 6 a liquid 15 rich in acidic gases is obtained, which is regenerated by expansion.

It is expanded in two steps through the valves 16 and 17 in the separators 18 and 19, from which the vapours 20 and 21, essentially constituted by methane and carbon dioxide, which are recycled to the tower 6 after being compressed in 22 and 23, are collected.

From the bottom of the separator 19 a liquid 24 is obtained, which is essentially constituted by the solvent and by the removed $CO_2$, the latter being vapourized by expansion through the valves 25 and 26, and heating in the heat exchange assembly 27. Said heat exchange assembly has been represented for simpleness' sake as one single exchanger, but in reality it supplies the cooling power necessary to the process (for example, in the heat exchangers 2, 8, 11).

Vapourized $CO_2$ is separated from the solvent in the separators 28 and 29, the first one being under a slight over-pressure, the second under vacuum, maintained by the vacuum pump 30, and is discharged from the plant in 31.

The regenerated solvent 32 outcoming from the bottom of the separator 29 is pumped by the pump 33 and mixed in 34 with the gas outcoming from the absorber tower. The mixture obtained is cooled in 35 and is separated in 36, the processed gas 37 being separated from the absorber solvent 38.

The solvent 38, after being pumped in 39, is mixed in 40 with the gas outcoming from the absorber tower 6; the mixture obtained is cooled in 41 and separated in 42, the treated gas 43, which is subsequently mixed in 34 with the regenerated solvent 32, being separated from the solvent 44, which is pumped by the pump 45 to the absorber tower 6.

An Example is now supplied by using the flow sheet of FIG. 1, to the purpose of better illustrating the invention, which Example is not to be considered as being limitative of the same invention.

EXAMPLE 1

A natural gas containing 80.85% by mol of $CO_2$, the balance being methane, available at $41°$ C. and under 63 abs. atm. in an amount of 33,584 kmol/h, is processed according to the flow sheet of FIG. 1, methane being obtained with a $CO_2$ amount of 2% by mol.

After the initial cooling in the exchangers 2, 8 and 11, the incoming fluid is expanded to 40 abs. atm. As the solvent, methyl acetate is used. The treated gas is produced under 40 abs. atm.

The circulation of solvent necessary to carry out the purification is of 134,000 kg/h.

COMPARATIVE EXAMPLE 2

The same natural gas as of Example 1 is processed according to the flow sheet of FIG. 2, which represents a process of the prior art. In said flow sheet the regenerated solvent 32 outcoming from the bottom of the separator 29 is pumped by the pump 33 and is mixed in 40 with the gas outcoming from the absorber tower. The mixture obtained is cooled in 41 and separated in 42, the treated gas 37 being separated from the solvent 44 which is pumped by the pump 45 to the absorber tower 6.

Still using methyl acetate as the solvent, a circulation of solvent of 389,000 kg/h is necessary to perform the purification.

We claim:

1. Cryogenic process for the removal of acidic gases from natural gases or from synthesis gases essentially comprising an absorption in one or more towers in order to reduce the content of acidic gases, a cooling carried out, in the case of one single absorber tower, upstream the same tower, or, in case of two absorber towers, between the same towers, a regeneration of the solvent or of the solvents used in the absorption, the solvent or the solvents used being selected among low molecular weight esters, alcohols and ethers, belonging to the following classes:

esters of alcohols of general formula $R_1COOR_2$, wherein $R_1$ and $R_2$ are alkyl groups of from 1 to 4 carbon atoms, equal to or different from each other, wherein one or more hydrogen atoms can be substituted by alcoholic groups;

esters of glycols of general formula

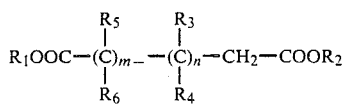

or

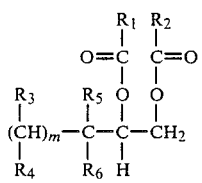

wherein $R_1$ and $R_2$ are alkyl groups having from 1 to 3 carbon atoms, equal to or different from each other, $R_3$, $R_4$, $R_5$, $R_6$, equal to or different from each other, are either alkyl groups containing from 1 to 3 carbon atoms or hydrogen atoms, m and n are integers which can have the value 0 or 1;

cyclic esters (lactones) of formula

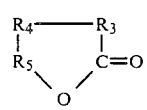

or

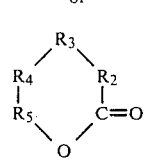

wherein $R_2$, $R_3$, $R_4$, $R_5$, equal to or different from each other, are alkylene groups wherein one or more hydrogen atoms can also be substituted by alkylic, alcoholic or ether groups;

alcohols of general formula

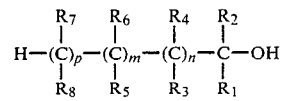

wherein $R_1$, $R_2$, $R_3$, $R_4$, $R_5$, $R_6$, $R_7$, $R_8$, equal to or different from each other, are alkyl groups having from 1 to 3 carbon atoms or hydroxy groups or hydrogen atoms, m, n and p are integers which can assume the values 0 and 1;

cyclic ethers such as

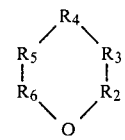

wherein $R_2$, $R_5$, $R_6$, equal to or different from each other, are alkyl groups wherein hydrogen can also be substituted by alkyl or methoxy groups, $R_3$ is either an oxygen atom or an alkylene group wherein hydrogen can also be substituted by alkyl or methoxy groups, $R_4$ is either equal to $R_3$ or can be absent in case of a pentaatomic ring;

ethers of general formula

wherein $R_1$ is an alkyl group of from 1 to 4 carbon atoms, $R_2$ is either an alkyl group of from 1 to 4 carbon atoms or a hydrogen atoms, $R_3$ is either an alkylene group or $(CH_2-O-CH_2)$, n is an integer which can have the value 0 or 1;

ethers of general formula

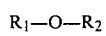

wherein $R_1$ and $R_2$, either equal to or different from each other, are alkyl groups of from 1 to 4 carbon atoms, wherein one or more hydrogen atoms can be substituted by alcoholic groups;

ester-ethers, compounds containing both the functions, of formula:

wherein $R_3$ and $R_4$, equal to or different from each other, are alkyl groups having from 1 to 4 carbon atoms, $R_2$ is an alkylene group having from 1 to 4 carbon atoms, $R_1$ is either equal to $R_2$ or equal to $R_3$, m and n are integers which can have the value 0 or 1, characterized in that the gas outcoming from one or more of the absorber towers is mixed once or more times with the solvent or solvents, the mixtures thus formed being then cooled, the solvent or solvents being thus separated from the same gas.

2. Process according to claim 1, wherein the mixings between the gas outcoming from the absorber tower or towers and the solvent or solvents are carried out be feeding them in countercurrent to each other.

3. Process according to claim 1, wherein the mixings between the gas outcoming from the absorber tower or towers and the solvent or solvents are in a number of at least two for each gas outcoming from an absorber tower.

4. Process according to claim 3, wherein for each gas outcoming from an absorber tower, the first mixing is carried out by mixing the treated gas with the regenerated solvent or solvents, to said mixing a cooling and a separation of the mixture obtained follows, the rated solvent or solvents being iseparated from the gas, which regenerated solvent or solvents is/are mixed in its/their turn in a second mixing step with the gas outcoming from the absorber tower, to which second mixing a cooling and a separation follows of the mixture obtained, thus the solvent or solvents, which is/are fed to the absorber tower, being separated from the gas, which is sent to the first mixing.

5. Process according to claim 4, wherein the two coolings following the two mixings are carried out at the same temperature or at different temperatures comprised within a temperature range of from −30° C. to −100° C.

6. Process according to claim 5, wherein the two coolings following the two mixings are carried out at the same temperature or at different temperatures comprised within a temperature range of from −40° C. to −80° C.

* * * * *